United States Patent [19]
van't Riet et al.

[11] Patent Number: 4,623,659

[45] Date of Patent: Nov. 18, 1986

[54] POLYHYDROXYBENZOIC ACID DERIVATIVES

[76] Inventors: Bartholomeus van't Riet, 3419 Noble Ave., Richmond, Va. 23222; Howard L. Elford, 3313 Gloucester Rd., Richmond, Va. 23227; Galen L. Wampler, 6938 Chamberlayne Rd., Mechanicsville, Va. 23111

[21] Appl. No.: 497,370

[22] Filed: May 23, 1983

[51] Int. Cl.[4] .................. A61K 31/215; A61K 31/15; A61K 31/155; C07C 123/00; C07C 131/00

[52] U.S. Cl. ..................................... 514/508; 514/519; 514/617; 514/633; 514/637; 558/6; 558/423; 564/177; 564/229; 564/247

[58] Field of Search ................ 564/229, 247; 424/326, 424/327; 512/508, 633, 637

[56] References Cited

U.S. PATENT DOCUMENTS

| | | | |
|---|---|---|---|
| 2,849,480 | 8/1958 | Kreuchenas | 560/17 |
| 3,629,443 | 12/1971 | Lafon | 424/326 |
| 4,236,322 | 4/1981 | van't Riet et al. | 424/324 |

OTHER PUBLICATIONS

Kirchner, Ewald *Chemical Abstracts* vol. 74 (1971) #141, 214n.

Clark, N. G. *Modern Organic Chemistry*, (1964) at p. 487, Oxford Univ. Press., Publ.

March, Jerry *Advanced Organic Chemistry* (1969) pp. 503–504, McGraw-Hill, Publ.

Tieman, Ferd. et al. *Berichte der Deutschen Chemischen Gesellschaft* vol. 17 (1884) at pp. 1685–1686.

Wagner and Briel, *Pharmazie*, 37, 251 (1982).

van't Riet et al., *J. Med. Chem.*, 22, 589 (1979).

Elford et al., *Can. Res.* 39, 844 (1979).

Gasparini et al., *Chem. Abstr.* 74, 112752f (1971).

Hasui, et al., *Chem. Abstr.* 81, 120190f (1974).

Yasuda et al., *Chem. Abstr.* 85, 94115w (1976).

Gale & Carnes, *Biochem. Pharm.*, 20, 2677 (1971).

Gale et al., *J. Med. Chem.*, 13, 571 (1970).

Howle & Gale, *Proc. Soc. Exp. Biol. Med.*, 131, 697 (1970).

Gale & Hynes, *J. Med. Chem.*, 11, 191 (1967).

Gale, *Proc. Soc. Exptl. Biol. Med.*, 122, 1236 (1966).

Elford et al., *Advances in Enzyme Regulation*, 19, 151 (1981).

van't Riet et al., *J. Pharm. Sci.*, 69, 856 (1980).

Child et al., *Can. J. Microbiol.*, 17, 1455 (1971).

Elford et al., *AACR Abstracts*, 1978, No. 250.

Elford et al., *AACR Abstracts*, 1977, No. 707.

Elford et al., *AACR Abstracts*, 1979, No. 601.

*Primary Examiner*—Natalie Trousof
*Assistant Examiner*—L. Hendriksen
*Attorney, Agent, or Firm*—Charles W. Ashbrook; James L. Rowe

[57] ABSTRACT

Polyhydroxy-substituted benz, phenylacet and mandelamidines, amidates, amidoximes and hydroxyamidoximes—ribonucleotide reductase inhibitors, and free radical scavengers.

16 Claims, No Drawings

POLYHYDROXYBENZOIC ACID DERIVATIVES

BACKGROUND OF THE INVENTION

Various hydroxy substituted benzohydroxamic acids are known—see Gale and Hynes, *J. Med. Chem.*, 11, 191 (1968), Gale, Hynes and Smith, ibid, 13, 571 (1970), Van't Riet et al., U.S. Pat. No. 4,263,322, Howle and Gale, *Proc. Soc. Exptl. Biol. Med.*, 131, 697 (1969), Gale et al. *Biochem. Pharm.*, 20, 2677 (1971).

Biological effects of hydroxy-substituted benzamides as well as other uses of such compounds are to found in Kreuchunas, U.S. Pat. No. 2,849,480, *Chemical Abstracts*, 85, 94115w (1978), 74, 112752f (1971).

The hydroxybenzohydroxamic acids are known to be inhibitors of ribonucleotide reductase according to the Elford, Wampler and Van't Riet group—see *Cancer Res.*, 22, 589 (1979), Abstracts, *Proc. Am. Assoc. Cancer Res.*, 18, 177 (1977), 19, 63 (1978), 20, 149 (1979), 22, 18 (1981), 23, 202 (1982), *Va. J. Sci.*, 29, 81 (1978), papers, *J. Pharm. Sci.*, 69, 856 (1980), New Approaches to the Design of Antineoplastic Agents-Bardos and Kalman, eds. pp 227 (Elsevier Biomedical, New York, N.Y.), 856 (1982), *Advances in Enzyme Regulation*, 19, 151 (1981), Abstract, *Med. Ped. Oncol.*, 10 102 (1982), Abstract, *Proc. 13th Int. Cancer Cong.* pp 88 (1982), papers, *J. Med. Chem.*, 22, 589 (1979) and *Cancer Treat. Rep.*, 66, 1825 (1982).

Polyhydroxy-substituted benzamidoximes, benzamidines, benzohydroxyamidoximes and benzamidates, so far as can be ascertained, are not recorded in the chemical literature.

SUMMARY OF THE INVENTION

This invention provides compounds of the formula:

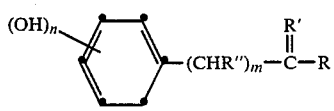

wherein n is 2–5, m is 0 or 1, R' is NOH or NH, R is $NH_2$ or NHOH when R' is NOH, R is $NH_2$ or $O-C_{1-3}$ alkyl when R' is NH, and R" is H or OH; and pharmaceutically acceptable acid addition salts thereof.

Preferred compounds according to formula I are those in which at least two of the hydroxyls in the phenyl ring are vicinal. An even more preferred group of compounds are those in which the vicinal hydroxyls are at C-3 and C-4 of the phenyl ring.

Compounds according to I are named as hydroxy-substituted benzamidoximes when m is O, R' is NOH and R is $NH_2$, as hydroxy-substituted benzohydroxyamidoximes when m is O, R' is NOH and R is NHOH, as hydroxy-substituted benzamidates when m is O, R' is NH and R is $O-C_{1-3}$ alkyl and as hydroxy-substituted benzamidines when m is O, R' is NH and R is $NH_2$.

When m is 1, and R" is OH, the compounds are named as hydroxy-substituted mandelamidoximes, mandelohydroxyamidoximes, mandelamidates and mandelamidines respectively. These mandelic acid derivatives have a center of assymetry and hence are prepared as a racemate or dl mixture. This invention includes both the racemates as well as the individual component optical isomers.

When m is 1 and R" is H, the compounds are named as hydroxy-substituted phenylacetamidoximes, phenylacetohydroxyamidoximes, phenylacetamidates and phenylacetamidines respectively.

Representative compounds according to formula I above include:

2,3-dihydroxybenzohydroxyamidoxime
3,4-dihydroxybenzohydroxyamidoxime
methyl 2,3,4-trihydroxybenzamidate
isopropyl 3,5-dihydroxybenzamidate
ethyl 3,4,5-trihydroxybenzamidate
ethyl 3,4-dihydroxybenzamidate
3,4-dihydroxybenzamidoxime
3,4,5-trihydroxybenzamidoxime
2,3,5-trihydroxybenzamidoxime
n-propyl 2,4,5-trihydroxybenzamidate
2,3-dihydroxybenzamidoxime
ethyl 2,4-dihydroxybenzamidate
ethyl 3,4,5-trihydroxybenzamidate
2,5-dihydroxybenzohydroxyamidoxime
3,4,5-trihydroxybenzamidine
2,3-dihydroxybenzamidine
2,3,4-trihydroxybenzamidine
3,4-dihydroxybenzamidine
dl-2,4,5-trihydroxymandelamidine
2,4,5-trihydroxybenzamidine
3,5-dihydroxybenzamidine
dl-3,4-dihydroxymandelamidine
dl-3,4,5-trihydroxymandelamidine
dl-2,3-dihydroxymandelamidine
dl-2,3,4-trihydroxymandelohydroxyamidoxime
dl-2,4,5-trihydroxymandelohydroxyamidoxine
2,3,4-trihydroxybenzamidoxime
2,3,4-trihydroxybenzohydroxyamidoxime
3,4,5-trihydroxybenzohydroxyamidoxime
ethyl 2,3-dihydroxybenzamidate
dl-3,4-dihydroxymandelamidoxime
dl-3,4,5-trihydroxymandelohydroxyamidoxime
dl-3,5-dihydroxymandelohydroxyamidoxime
dl-3,4-dihydroxymandelohydroxyamidoxime
dl-2,4-dihydroxymandelamidoxime
dl-2,3-dihydroxymandelamidoxime
dl-3,5-dihydroxymandelamidoxime
dl-2,3,4-trihydroxymandelamidoxime
dl-3,4,5-trihydroxymandelamidoxime
dl-2,4,5 -trihydroxymandelamidoxime
dl-methyl 3,4-dihydroxymandelamidate
dl-ethyl 3,5-dihydroxymandelamidate
dl-n-propyl 2,3-dihydroxymandelamidate
dl-methyl 2,3,4-trihydroxymandelamidate
dl-ethyl 3,4,5-trihydroxymandelamidate
dl-ethyl 2,3,5-trihydroxymandelamidate
dl-isopropyl 2,4,5-trihydroxymandelamidate
3,4-dihydroxyphenylacetamidoxime
3,5-dihydroxyphenylacetamidoxime
2,3-dihydroxyphenylacetamidoxime
2,5-dihydroxyphenylacetamidoxime
2,4-dihydroxyphenylacetamidoxime
2,3,4-trihydroxyphenylacetamidoxime
3,4,5-trihydroxyphenylacetamidoxime
2,4,5-trihydroxyphenylacetamidoxime
2,3,5-trihydroxyphenylacetamidoxime
ethyl 3,4-dihydroxyphenylacetamidate
methyl 2,3-dihydroxyphenylacetamidate
n-propyl 3,5-dihydroxyphenylacetamidate
isopropyl 2,3,4-trihydroxyphenylacetamidate
methyl 3,4,5-trihydroxyphenylacetamidate
methyl 2,4,5-trihydroxyphenylacetamidate
methyl 2,3,4,5-tetrahydroxyphenylacetamidate
ethyl 2,3,4,6-tetrahydroxyphenylacetamidate methyl 2,3,4,5,6-pentahydroxyphenylacetamidate
2,3,4,5-tetrahydroxyphenylacetamidine
2,3,4,6-tetrahydroxybenzylacetamidine
2,3,5,6-tetrahydroxyphenylacetamidine
2,3,4,5,6-pentahydroxyphenylacetamidine
2,3,4,5,6-pentahydroxyphenylacetohydroxyamidoxime
2,3,5,6-tetrahydroxyphenylacetohydroxyamidoxime
2,3,4,5-tetrahydroxyphenylacetohydroxyamidoxime
ethyl 2,3,5-trihydroxyphenylacetamidate
2,3-dihydroxyphenylacetamidine
3,4-dihydroxyphenylacetamidine
3,5-dihydroxyphenylacetamidine
2,4-dihydroxyphenylacetamidine
2,5-dihydroxyphenylacetamidine
2,3,4-trihydroxyphenylacetamidine
3,4,5-trihydroxyphenylacetamidine
2,4,5-trihydroxyphenylacetamidine
2,3,5-trihydroxyphenylacetamidine
3,4-dihydroxyphenylacetohydroxyamidoxime
3,5-dihydroxyphenylacetohydroxyamidoxime
2,3-dihydroxyphenylacetohydroxyamidoxime
2,3,4-trihydroxyphenylacetohydroxyamidoxime
2,3,5-trihydroxyphenylacetohydroxyamidoxime
2,4,5-trihydroxyphenylacetohydroxyamidoxime
3,4,5-trihydroxyphenylacetohydroxyamidoxime,
and the like.

Benzamidoximes and phenylacetamidoximes according to I above, where R' is NOH and R is NH₂, can be prepared reacting a nitrile of the formula

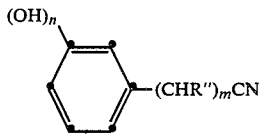

where m is 0 or 1 and R" is H with hydroxylamine in aqueous solution. Where R" is OH and m is 1, this nitrile may be a transitory intermediate formed by reacting an aldehyde of the formula

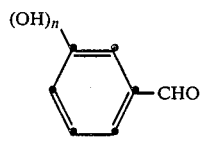

where n is 2–5 with a mixture of an alkali metal cyanide and hydroxylamine hydrochloride in aqueous solution. The mandelonitrile (a cyanohydrin) forms initially but then reacts at once with hydroxylamine to give the desired mandelamidoxime.

The amidates (I where R is O—C₁₋₃ alkyl and R' is NH) can be prepared by reacting the above nitrile (II) with a lower alkanol (C₁₋₃ alkylOH) to which has been added an acid such as gaseous HCl. The reaction medium here should be non-aqueous, and Lewis acids other than HCl can be employed.

Nitriles useful in the above two synthetic procedures are readily available by processes set forth in the art. 2,3,4-Trihydroxybenzonitrile, the three tetrahydroxybenzonitriles and pentahydroxybenzonitrile are, however, new and their synthesis will be set forth in detail below.

Compounds according to I in which R is NHOH and R' is NOH can be prepared from the corresponding benzamidoxime, phenylacetamidoxime or mandelamidoxime

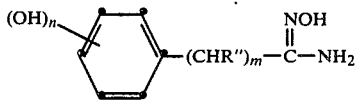

when n, m and R" have the same significance as before by reaction with hydroxylamine hydrochloride. The hydroxy-substituted benzamidines, phenylacetamidines and mandelamidines can be prepared from the corresponding amidate by reaction with ethanolic ammonia.

The following more detailed examples illustrates the preparation of the compounds of this invention. Other equally useful methods for their preparation will readily suggest themselves to those skilled in the art.

EXAMPLE 1

Preparation of 3,4-Dihydroxybenzamidoxime 30 g. of 3,4-Dihydroxybenzonitrile were dissolved in 300 ml. of water containing 25 g. of hydroxylaminesulfate which has been neutralized by the addition of aqueous sodium hydroxide to pH=8.0. The reaction mixture was stirred at about 45° C. for 18 hours. 3,4-Dihydroxybenzamidoxime formed in the above reaction had precipitated and was collected by filtration. The filtered amidoxime was suspended in water and the aqueous suspension acidified to about pH=2.0 and 12N aqueous hydrochloric acid. The acidic solution was decolorized with charcoal and the solvent removed by evaporation. Recrystallization of the residue yielded 3,4-dihydroxybenzamidoximehydrochloride melting at about 193° C. with decomposition.

Analysis Calculated: C, 41.09; H, 4.43; N, 13.69; Found: C, 41.12; H, 4.47; N, 13.69.

Equivalent weight by titration 206 (theory=204.6); yield=72%.

EXAMPLE 2

Preparation of 3,4,5-Trihydroxybenzamidoxime

About 7.5 g. of 3,4,5-trihydroxybenzonitrile were dissolved in 200 ml. of water containing 7 g. of hydroxylamine sulfate which solution had previously been neutralized to about pH=8.0 with aqueous sodium hydroxide. 2 g. of sodium sulfite were also present in solution. The reaction mixture was stirred at 45° C. for about 18 hours after which time the precipitated 3,4,5-trihydroxybenzamidoxime formed in the above reaction was collected. The product was converted to the hydrochloride salt and the hydrochloride salt purified by the process of Example 1. 3,4,5-Trihydroxybenzamidoxime hydrochloride thus prepared melted with decomposition at a temperature of about 206° C. after recrystallization from an isopropanol-ethyl acetate solvent mixture.

Analysis Calculated: C, 38.11; H, 4.11; N, 12.72; Found: C, 38.16; H, 4.16; N, 12.66.

Equivalent weight by titration with aqueous sodium hydroxide=220 (theory=220.6); yield=80%.

EXAMPLE 3

Preparation of Ethyl 3,4,5-Trihydroxybenzamidate 5 g. of 3,4,5-Trihydroxybenzonitrile were dissolved in ether. 2.2 ml. of ethanol were added. Next, anhydrous gaseous hydrogen chloride was passed through the solution. Ethyl 3,4,5-trihydroxybenzamidate hydrochloride formed in the above reaction precipitated. The precipitate was recrystallized from an isopropanolether solvent mixture. Ethyl 3,4,5-trihydroxybenzamidate hydrochloride thus prepared and purified melted at about 72° C. with decomposition.

Analysis Calculated: C, 46.26; H, 5.18; N, 5.99; Found: C, 46.26; H, 5.22; N, 6.00.

Equivalent weight by titration with sodium hydroxide = 115.5 (theory = 116.8); yield = 78%.

Ethyl 3,4,5-trihydroxybenzamidate can be prepared by neutralization of the hydrochloride salt, extraction of the ester into ether and removal of the ether by evaporation.

EXAMPLE 4

Preparation of Ethyl 3,4-Dihydroxybenzamidate

Following the procedure of Example 3, 3,4-dihydroxybenzonitrile was converted to ethyl 3,4-dihydroxybenzamidate hydrochloride by the reaction with ethanol in the presence of hydrogen chloride. The compound melted at 170° C. with decomposition after recrystallization from an isopropanol/ether solvent mixture; yield = 65%.

Analysis Calculated: C, 49.67; H, 5.66; N, 6.44; Found: C, 49.91; H, 5.61; N, 6.45.

EXAMPLE 5

Preparation of Gallamidine

About 4.5 g. of ethyl 3,4,5-trihydroxybenzamidate hydrochloride were heated with an excess of 14N aqueous ammonium hydroxide in ethanol solution. The volatile constituents were removed by evaporation and the residue, comprising gallamidine formed in the above reaction, was dissolved in alcohol. Gallamidine free base was converted to the hydrochloride salt by passing gaseous hydrogen chloride into the alcoholic solution. Gallamidine hydrochloride melted at about 169° C. with decomposition after recrystallization from an ethanol/ethyl acetate solvent mixture; yield = 53%.

Equivalent weight = 203 by titration with aqueous sodium hydroxide (theory 204.5).

Analysis Calculated: C, 41.09; H, 4.43; N, 13.69; Found: C, 40.80; H, 4.47; N, 14.30.

EXAMPLE 6

Preparation of 3,4-Dihydroxybenzohydroxyamidoxime

A solution of 5.5 g. of 3,4-dihydroxybenzamidoxime (from Example 1) was prepared in a minimal quanitity of methanol. 3.5 g. of hydroxylamine hydrochloride were added. The reaction mixture was allowed to stand for about one day at about 50° C. Volatile constitutents were removed by evaporation. Ethyl acetate was added to the residue. The resulting precipitate was separated by filtration and gaseous hydrogen chloride passed into the filtrate. 3,4-Dihydroxybenzohydroxyamidoxime hydrochloride thus prepared was separated by filtration. The compound melted at about 169° C. with decomposition.

Equivalent weight by titration with sodium hydroxide = 219 (theory = 220.5)

Analysis Calculated: C, 38.11; H, 4.11; N, 12.70; Found: C, 38.28; H, 4.15; N, 12.61.

EXAMPLE 7

Preparation of 3,4-Dihydroxymandelamidoxime

Seven and eight-tenths grams of 3,4-dihydroxybenzaldehyde were added to 100 ml. of an aqueous solution held at −15° C. containing 7.8 g. of hydroxylamine hydrochloride and 5.5 g. of sodium cyanide. The reaction mixture was stirred overnight at about 0° C. and then filtered. Four g. of 3,4-dihydroxymandelamidoxime monohydrate formed in the above reaction were obtained melting at 151° C. with decomposition (after loss of water of crystallization at about 120° C.) yield = 36%.

Analysis Calculated: C, 44.44; H, 5.60; H, 12,96; Found: C, 44.37; H, 5.65; N, 12.92.

EXAMPLE 8

Preparation of 2,3,4-Trihydroxybenzamidoxime

Following the procedure of Example 2, 3.5 g. of 2,3,4-trihydroxybenzonitrile were reacted in 60 ml. of water with 4 g. of hydroxylamine sulfate and 2 g. of sodium bisulfite at pH = 8.0 (adjusted by addition of concentrated aqueous sodium hydroxide). The reaction mixture was maintained at ambient temperature for about one hour and was then cooled. 2,3,4-Trihydroxybenzamidoxime precipitated and the precipitate was collected by filtration. The filter cake was dissolved in dilute aqueous hydrochloric acid and the resulting solution filtered through activated charcoal. Evaporation of the volatile constituents from the filtrate under reduced pressure yielded 2,3,4-trihydroxybenzamidoxime as a hydrochloride salt, melting at 207° C. with decomposition after recrystallization from a methanol/ethyl acetate solvent mixture; yield = 9%.

Analysis Calculated: C, 38.11; H, 4.11; N, 12.72; Found: C, 37.34; H, 4.06; N, 12.43.

The preparation of nitrile starting materials useful for preparing most of the compounds of this invention where the amide starting material is available or known is illustrated in the following example.

Preparation I

Preparation of Nitrile Starting Materials

A reaction mixture containing 23.5 g. of gallamide, 180 ml. of ethyl acetate and 35 ml. of thionylchloride was refluxed for about 18 hours. The volatile contents were removed by evaporation in vacuo and the resulting residue dissolved in 215 ml. of water. This aqueous solution was heated to about 90° C. until the evolution of gas had ceased. The aqueous solution was filtered through charcoal and the water removed from the filtrate by evaporation. 18 g. of gallonitrile were obtained melting at about 219° C. with decomposition (86% yield). Other nitriles useful as starting materials can be prepared similarly.

Preparation II

Preparation of 2,3,4-Trihydroxybenzonitrile

Eighteen and five tenths grams of 2,3,4-trihydroxybenzamide were refluxed with 20 ml. of phosphorusoxychloride and 100 ml. of ethyl acetate for 2.5 hours. The volatile constituents were removed in vacuo and the residue poured into 150 ml. of an ice-water mixture. The resulting suspension was heated to 95° C. and then filtered through activated carbon. The filtrate was concentrated to about 50 ml. whereupon 2,3,4- trihydroxybenzonitrile precipitated and was collected by filtration. 2,3,4-Trihydroxybenzonitrile monohydrate thus prepared melted at 172° C. after recrystallization from a methanol-benzene solvent mixture; yield=57%.

Analysis Calculated: C, 49.71; H, 4.17; N, 8.28; Found: C, 49.70; H, 4.17; N, 8.27.

Preparation III

Preparation of 2,3,4,5-Tetrahydroxybenzonitrile

Following the procedure of Mayer et al., Chem. Ber., 89, 511 (1956), 3,4,5-trimethoxybenzoic acid was brominated in ethyl acetate solution without added water using only 40% of the chloroform volume specified in that reference. Twenty-three and five tenths grams of 2-bromo-3,4,5-trimethoxybenzoic acid thus synthesized were added to a solution prepared by dissolving 1 g. of cupric acetate and 5 g. of sodium sulfite in 110 ml. of water followed by 27 g. of sodium hydroxide. The reaction mixture, which was a suspension, was heated to boiling for about six hours. Since it showed a tendency to solidify, extra water was added to maintain fluidity. At the end of six hours, the suspension was poured into a mixture of ice and 120 ml. of 12N aqueous hydrochloric acid. The volume was raised to about 900 ml. with water. This mixture was then heated. Complete dissolution occurred at about 95° C. at which point, 700 mg. of thioacetamide were added and heating continued until black copper sulfide had formed. The mixture was filtered through carbon. 3,4,5-Trimethoxysalicylic acid monohydrate precipitated from the filtrate.

The corresponding methyl ester was prepared by heating 3,4,5-trimethoxysalicylic acid monohydrate in methanol containing 2% sulfuric acid, as set forth in the above reference.

Methyl 3,4,5-trimethoxysalicylate prepared as above was heated in 14N aqueous ammonium hydroxide for four hours. The volatile constituents were removed in vacuo and the resulting residue, 3,4,5-trimethoxysalicylamide, was recrystallized from water at pH=5.0. The compound melted at about 151° C.; yield=70% (13.4 g. of 3,4,5-trimethoxy salicylic acid gave 9.3 g. of pure 3,4,5-trimethoxysalicylamide.) Seven and seven tenths grams of 3,4,5-trimethoxysalicylamide were heated to reflux with 8 ml. of phosphorusoxychloride in 100 ml. of ethyl acetate for about one hour. The volatile constituents were removed by evaporation in vacuo and the residue, comprising 3,4,5-trimethoxysalicylnitrile, was dissolved in water to which some ethanol was added until the solution was clear at 95° C. Again the volatile constituents were removed in vacuo and the liquid residue dissolved in hot benzene. The residue was dried and the solution used in the next demethylation step without further purification.

The above benzene solution was diluted to 100 ml. with benzene and 20 g. of anhydrous aluminum chloride added. The reaction mixture was heated to reflux temperature for two hours and the suspension poured into a mixture of 12N hydrochloric acid and ice. The volatile constituents were removed from this mixture by evaporation and 2,3,4,5-tetrahydroxybenzonitrile, formed in the above reaction, was extracted into ethyl acetate. The ethyl acetate extract was dried and the residue obtained by removal of the ethyl acetate was recrystalized from water. Three grams of 2,3,4,5-tetrahydroxybenzonitrile were obtained which decomposed at 219° C. yield=36% from the starting 3,4,5-trimethoxysalicylamide.

Analysis Calculated (for one-fourth mole of water): C, 48.99; H, 3.02; N, 8.16; Found: C, 49.06; H, 3.23; N, 8.14.

2,3,4,5-tetrahydroxybenzamide was prepared by careful hydrolysis of the corresponding nitrile in concentrated hydrochloric acid at 60° C. The amide gradually precipitated from a solution of 1.5 g. of the nitrile in 25 ml. of hydrochloric acid. After recrystallization from water, the product decomposed at 290° C. Yield=23%.

Analysis Calculated: C, 45.41; H, 3.81; N, 7.56; Found: C, 44.83; H, 3.88; N, 7.27.

The above procedure can be adapted for the preparation of other tetrahydroxybenzonitriles, although isomer separation procedures may be necessary where two monobromo substitution products are possible in the starting trimethoxybenzoic acid. Thus, 2,3,5,6-tetrahydroxybenzonitrile can be prepared from 2,3,5-trimethoxybenzoic acid (with 2,3,4,5-tetrahydroxybenzonitrile as a contaminant). Likewise, 2,3,4,6-tetrahydroxybenzonitrile can be prepared from 2,3,4-trimethoxybenzonic acid.

PREPARATION IV

Preparation of Pentahydroxybenzonitrile

Eleven and three-tenths grams of pentamethoxybenzamide obtained by the procedure of Dallacher, Ann., 665, 78–83 (1963) were dissolved in 50 ml. of ethyl acetate to which 10 ml. of thionyl chloride had been added. The reaction mixture was heated to reflux for about three hours. Evaporation of volatile constituents in vacuo yielded a residue comprising pentamethoxybenzonitrile melting at 64° C. after recrystallization from methanol/water; yield=80%

Analysis Calculated: C, 56.92; H, 5.97; N, 5.53; Found: C, 56.92; H, 5.88; N, 5.49.

Four and three-tenths grams of pentamethoxybenzonitrile were refluxed in 12.5 g. of anhydrous aluminum chloride and 125 ml. of toluene for three hours after which time the suspension was poured into a mixture of 50 ml. of 12N aqueous hydrochloric acid and 200 g. of ice. The toluene layer was separated and the product recovered from the aqueous layer by filtration. Recrystallization from an ethyl acetate/toluene solvent mixture yielded pentahydroxybenzonitrile decomposing at 238° C. with a prior slight decomposition at 220° C.; yield =66%.

Analysis calculated (for monohydrate): C, 41.80; H, 3.51; N, 6.96; Found: C, 42.20; H, 3.54; N, 6.94.

Following the procedure of Example 3, ethyl tetrahydroxybenzamidate can be prepared from the corresponding nitrile.

Also following the above procedure, pentahydroxybenzamidate can be prepared from the corresponding pentahydroxybenzonitrile by reaction with ethanol in the presence of anhydrous HCl. The compound is converted to the hydrochloride salt and isolated as such according to the procedure of Example 3.

Compounds represented by formula I above have the ability to inhibit ribonucleotide reductase, an enzyme involved in the reductive conversion of ribonucleotides to deoxyribonucleotides. This enzymatic reaction is a rate controlling step in the biosynthetic pathway leading to DNA and cell replication. In general, the ribonucleotide reductase level is closely correlated with cellular replication. Thus, it is not surprising that the compounds of this invention, which are potent ribonucleotide reductase inhibitors, are also capable of prolonging the life of mice carrying transplanted tumors since replication of tumor cells is equally inhibited. In particular, we have found that administration of a compound of this invention coming within the scope of formula I above prolongs the life of mice inoculated with L1210 leukemia, a tumor not ordinarily susceptible to chemotherapy. In addition, the compounds have shown activity against P388 leukemia and B16 melanoma.

The results of biological tests of compounds according to formula I are incorporated in a series of Tables which follow. Table 1 gives ribonucleotide reductase data for representative compounds of formula I. In the table, column 1 gives the substitution pattern in the benzene ring, column 2, the $(CHR'')_m$ group, column 3, the $$\overset{R'}{\underset{\|}{C}}-R$$

group, and column 4, the $ID_{50}$ (inhibitory dose in micromolar concentration which inhibits ribonucleotide reductase by 50%) in μmoles.

TABLE 1

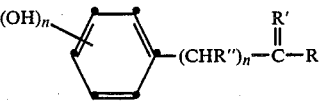

| $(OH)_n$ | $(CHR'')_m$ | $\overset{R'}{\underset{\|}{C}}-R$ | $ID_{50}$ μM |
|---|---|---|---|
| 3,4 | bond | NOH<br>∥<br>C—NH₂.HCl | 8 |
| 3,4 | bond | NH<br>∥<br>C—OEt.HCl | 12 |
| 3,4 | bond | NH<br>∥<br>C—NH₂.HCl | 20 |
| 3,4 | bond | NOH<br>∥<br>C—NHOH.HCl | 40 |
| 3,4,5 | bond | NOH<br>∥<br>C—NH₂.HCl | 5 |
| 3,4,5 | bond | NH<br>∥<br>C—OEt.HCl | 15 |
| 3,4,5 | bond | NH<br>∥<br>C—NH₂.HCl | 25 |
| 3,4 | CHOH | NOH<br>∥<br>C—NH₂.H₂O | 10 |
| 3,4,5 | bond | NOH<br>∥<br>C—NHOH.HCl | 25 |
| 2,3,4 | bond | NOH<br>∥<br>C—NH₂.HCl | 7 |

TABLE 1-continued

| $(OH)_n$ | $(CHR'')_m$ | $\overset{R'}{\underset{\|}{C}}-R$ | $ID_{50}$ μM |
|---|---|---|---|
| 2,3 | bond | NOH<br>∥<br>C—NH₂.HCl | 18 |

In the above determination of $ID_{50}$'s in Table 1, ribonucleotide reductase is partially purified from HeLa cells or Ehrlich ascites cells by a procedure similar to that set forth by Elford et al. *J. Biol. Chem.*, 245, 5228 (1970). The activity of the enzyme was measured by a slightly modified assay procedure originally developed by Reichard et al. id, 236, 1150 (1969). This procedure measures the conversion of CDP to dCDP. The assay mixture (0.34 ml.) contains 3 μCi of [³H] CDP (specific activity 14–19 Ci/μmol), 3.3 μmole ATP, 5.9 μmoles magnesium chloride, 8.8 μmoles Hepes buffer at pH=7.5, 15 μmoles dithiothreitol and enzyme protein between 0.4 and 1.3 mg. Incubation was provided for forty minutes at 30° C. Ion exchange chromatography employing Dowex 50 (H⁺) resin is used to separate the product from the substrate. The inhibitors were dissolved in water and a mixture of water and up to 1% ethanol or 2% dimethylsulfoxide, neither one of which inhibitied the enzyme at these concentrations. Each inhibitor was tested at a minimum of three concentrations and the active compounds reassayed at least one additional time. $ID_{50}$'s (μmolar) were estimated from graphs summarizing results for each compound.

Testing of the compound of this invention against L-1210 lymphoid leukemia were carried out as follows: L-1210 leukemia was maintained by weekly passage of 10⁵ L-1210 cells intraperitoneally into DBA/2 mice. Diluted ascitic fluid, 0.1 ml. (10⁵ cells), was administered ip to female B6D₂F₁ mice weighing about 20 g. Drugs were administered ip 24 hours after tumor transplantation and injections were continued daily for a total of eight days. A group of control mice receiving only the injection medium were maintained. Table 2 which follows gives the antitumor activity against L-1210 leukemia for certain compounds of this invention. In the table, column 1 gives the name of the compound, column 2 the dose in mg./kg., and column 3 the percent increase in survival time over controls at each dose level.

TABLE 2

ANTITUMOR ACTIVITY IN L1210 LEUKEMIA

| Name of Compound | Dose in mg/kg | % Increase in Survival Time |
|---|---|---|
| 3,4-dihydroxybenzamidoxime - HCl | 157 | 132.0 |
| | 200 | 43.5 |
| | 238 | 46.9 |
| | 300 | 73.9 |
| 3,4,5-dihydroxybenzamidoxime - HCl- | 59 | 90.0 |
| | 132 | 54.5 |
| | 196 | toxic |
| | 220 | 63.6 |
| | 275 | 30.6 |
| 2,3,4-trihydroxybenzamidoxime - HCl | 100 | 38.9 |
| | 200 | 36.1 |
| | 218 | 67.7 |

TABLE 2-continued

ANTITUMOR ACTIVITY IN L1210 LEUKEMIA

| Name of Compound | Dose in mg/kg | % Increase in Survival Time |
|---|---|---|
| | 300 | toxic |
| ethyl 3,4-dihydroxybenzamidate - HCl | 218 | toxic |
| | 327 | toxic |
| | 435 | toxic |
| ethyl 3,4,5-trihydroxybenzamidate - HCl | 300 | 42.3 |
| | 450 | 58.4 |
| 3,4-dihydroxybenzamidine - HCl | 52 | 26.8 |
| | 100 | 58.3 |
| | 104 | 34.1 |
| | 200 | 41.7 |
| | 300 | 47.2 |
| | 400 | 47.8 |
| | 603 | 83.0 |
| 3,4,5-trihydroxybenzamidine - HCl | 200 | 43.5 |
| | 300 | 10.2 |
| 3,4-dihydroxybenzohydroxy-amidoxime - HCl | 155 | 39.0 |
| | 200 | 47.8 |
| | 300 | 41.3 |
| 3,4,5-trihydroxybenzohydroxy-amidoxime - HCl | 100 | 47.2 |
| | 200 | 55.6 |
| | 300 | 63.9 |
| 3,4-dihydroxybenzohydroxymandel amidoxime - H$_2$O | 435 | 45.2 |
| | 606 | 45.2 |
| 2,3-dihydroxybenzamidoxime - HCl | 300 | toxic |

3,4-Dihydroxybenzamidoxime and 3,4,5-trihydroxybenzamidoxime were subjected to a further series of tests against various transplanted tumors in mice according to the following protocols:

For L-1210 lymphoid leukemia, 20 grams CDF$_1$ or BDF$_1$ mice rejected ip with 10$^5$ leukemia cells. The drug was given one day after tumor inoculation continued for an additional eight days. The mean survival time for the treated animal was compared to that of the control group. Table 3 which follows gives the results of this test for the above two compounds. In the table, column 1 gives the name of the compound, column 2 the dose levels, and column 3 treated over control percent survival time. (In other words, a figure of 175 indicates a 75% increase in survival time.)

TABLE 3

| Activity vs L-1210 Leukemia | | |
|---|---|---|
| Name of Compound | Dose mg/kg | t/c % |
| 3,4-dihydroxybenzamidoxime.HCl | 400 | toxic, 200*202 |
| | 300 | 113 |
| | 200 | 175,128,155,186 |
| | 100 | 128,132,141,133 |
| | 50 | 137,117,132,146 |
| | 25 | 130 |
| 3,4,5-trihydroxybenzamidoxime.HCl | 200 | 212,182 |
| | 100 | 152,137 |
| | 50 | 138,137 |
| | 25 | 136,121 |

*t/c % greater than 130 are significant

The drugs were also used to treat melanotic melanoma B$_{16}$. The protocol for testing against this tumor is as follows:

0.5 ml. of a tumor homogenate prepared by homogenizing 1 g. of tumor with 10 ml. of cold balanced solution is implanted ip in groups of 10 B$_6$C$_3$F$_1$ mice. The drug is administered daily for a total of nine days starting one day after tumor inoculation. The results are expressed as mean survival time of treated group versus control groups (T/C) as a percent. Table 4 which follows gives the results of this test.

TABLE 4

| Activity vs B$_{16}$ Melanoma | | |
|---|---|---|
| Name of Compound | Dose mg/kg | T/C % |
| 3,4-dihydroxybenzamidoxime.HCl | 400 | 117 |
| | 200 | 134 |
| | 100 | 129 |
| | 50 | 127 |
| | 25 | 119 |
| ethyl gallamidate | 800 | toxic |
| | 400 | 124,156,137 |
| | 200 | 121,125,122 |
| | 100 | 121,109,107 |
| | 50 | 109,104 |
| | 25 | 105 |

*T/C % greater than 120 are significant.

A compound of this invention was also tested on the solid colon tumor model, colon 38. The tumor was implanted subcutaneously and the drug injected intraperitoneally twice a day on day two (seven hours apart) and twice on day nine. The median tumor weight estimated from tumor diameter is the parameter of tumor inhibition and is measured on day 20. The median tumor weight of treated versus control=T/C percent. Table 5 which follows gives the results of this test.

TABLE 5

| Activity vs Colon 38 | | |
|---|---|---|
| Name of Compound | Dose mg/kg | T/C % |
| 3,4-dihydroxybenzamidoxime.HCl | 800 | 87 |

Lower doses were ineffective.

Compounds of this invention also showed some activity against P388 leukemia. The following protocol was used:

CDF$_1$ mice were injected ip with 10$^6$ cells. The drug was administered in the first day after tumor inoculation and continued daily for five treatments. The mean survival time of the treated group compared to the nontreated control group equals T/C×100=T/C percent. Table 6 which follows gives the results of these determinations.

TABLE 6

| Actvity vs P388 Leukemia | | |
|---|---|---|
| Name of Compound | Dose mg/kg | T/C % |
| 3,4,5-trihydroxybenzamidoxime.HCl | 400 | toxic |
| | 300 | 163 |
| | 200 | 155,155,177 |
| | 100 | 150,154,138,148 |
| | 50 | 142,138,141 |
| ethyl gallamidate | 400 | 149,160 |
| | 200 | 139,123 |
| | 100 | 129,128 |
| | 50 | 114 |
| | 25 | 112 |
| | 12.5 | 104 |

*T/C % over 130 are considered significant

It is believed that the antineoplastic activity of the compounds of this invention is due in part to their ability to scavenge free-radicals. Additionally, the compounds of this invention are cancer protective agents and this utility also may be a manifestation of their free-radical scavenging capability. Free-radical scavenging agents may also be useful in detoxifying mammals in whom an excess of free radicals is a cause and/or result of the toxicity. Other possible uses of free radical scavengers are to inhibit protaglandin transformation, leucotriene interconversion and lipogenesis, to act as inflammatory modulators and as food additive or preservatives to prevent lipid oxidation. The free radical scavenging ability of the compounds of the invention was determined by measuring the destruction of the stable free radical, diphenylpicrylhydrazyl, in the presence of the test compound in a manner similar to that reported by Venker and Herzmann, *Naturwiss*, 47, 133-134 (1960). The absorbance at 518 nM of a 100 µM solution of diphenylpicryhydrazyl free radical in acetone was monitored in a Gilford spectrophotometer. The test compound was added at a final concentration of 25 µM and the rate of reduction of absorption at 518 nM was observed. Table 7 below gives the free radical scavenging abilities of the compounds of this invention expressed as the initial rate of decrease in optical density units/min.

TABLE 7
FREE RADICAL SCAVENGING ABILITIES

| Compound | Initial Δ units/min.* (518 nm) |
|---|---|
| 3,4-dihydroxymandelamidoxime | 0.383 |
| 3,4-dihydroxybenzamidoxime.HCl | 0.718 |
| 3,4,5-trihydroxybenzamidoxime.HCl | 0.929 |
| Ethyl 3,4,5-trihydroxybenzamidate.HCl | 3.730 |
| Ethyl 3,4-dihydroxybenzamidate.HCl | 0.706 |
| 3,4-dihydroxybenzamidine.HCl | 1.721 |
| 3,4,5-trihydroxybenzohydroxyamidoxime.HCl | 0.882 |
| 3,4,5-trihydroxybenzamidine.HCl | 4.912 |

*One optical density unit decrease of initial absorbance/min at 518 nm by 2.5 µM of agent.

Additional free radical scavenging potential of a compound of this invention was measured on a generated tyrosine free radical. There is evidence that a tyrosine free radical is formed as part of the mammalian ribonucleotide reductase enzyme during the conversion of ribonucleotides to deoxyribonucleotides—see L. Äkerblom, et al. *Proc. Natl. Acad. Sci. USA*, 78, 2159-2163 (1981). The method for the generation of the tyrosine free radical and its destruction by a compound of this invention was accomplished by pulse radiolysis experiments at Brunel University, Oxbridge England on the Brunel 4 MeV linear accelerator using a 1.5 cm optical cell and a 200 ns pulse delivering a dose of approximately 1 krad as measured by thiocyanate dosimetry. All solutions were purged with nitrogen using a syringe-deaerating technique prior to use. The detailed description of the methodology can be found in R. L. Willson, *Chemistry and Industry*, 183-193 (1977).

For the generation of the tyrosine radical, sodium azide was utilized as an intermediate between the pulse radiolysis generated free electron and tyrosine. Hydroxyurea was used as a reference point for the ability of these compounds to scavange tyrosine free radical since hydroxyurea inhibition of ribonucleotide reductase has been attributed to its ability to scavenge the free radical of the active mammalian ribonucleotide reductase.—See Äkerblom et al (loc. cit). See also I. K. Larsen et al., *Eur. J. Biochem*, 125, 75-81 (1982). A rate constant of $1.9 \times 10^6 M^{-1} S^{-1}$ was determined for hydroxyurea and $4.5 \times 10^8 M^{-1} S^{-1}$ for 3,4-dihydroxybenzamidoxime hydrochloride. In other words, 3,4-dihydroxybenzamidoxime hydrochloride was 100+ times a faster scavenger of tyrosine free radical than hydroxyurea.

The novel nitriles and amide starting materials for the synthesis of the compounds of this invention, (Formula I wherein n is 4 or 5), although chiefly useful as intermediates, have ribonucleotide reductase activity and are also active free radical scavengers.

Table 8 which follows gives anti-tumor data vs L-1210 and P-388 leukemia for these novel nitriles.

TABLE 8
Antileukemia Activity

| Name of Compound | Dose in mg/kg | % Increase in Survival Time |
|---|---|---|
| L1210 | | |
| 3,4-dihydroxybenzonitrile | 47.6 | 4.7 |
| | 95.2 | 15.6 |
| | 196 | Toxic |
| 2,3,4-trihydroxybenzonitrile | 50 | 11.0 |
| | 100 | 26.0 |
| | 155 | 12.1 |
| | 259 | Toxic |
| | 327 | Toxic |
| 3,4,5-trihydroxybenzonitrile | 118 | 34.0 |
| | 157 | 28.0 |
| 2,3,4,5-tetrahydroxybenzonitrile | 163 | 48.4 |
| | 230 | Toxic |
| pentahydroxybenzonitrile | 34.3 | 14.2 |
| | 51.5 | 0 |
| | 77.2 | Toxic |
| | 116.0 | Toxic |
| P-388 | | |
| 3,4,5-trihydroxybenzonitrile | 400 | 26 |
| | 200 | 26,39 |
| | 100 | 10,39 |
| | 50 | 15,20 |

The compounds of this invention are administered parenterally to mammals suffering from a neoplastic disease, preferably using a water soluble salt of the drug. Intravenous injection of an isotonic salt solution of the drug salt is the preferred route of administration.

We claim:

1. A compound of the formula

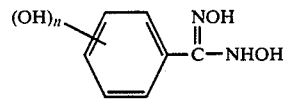

in which n is 2-5 or a pharmaceutically acceptable acid addition salt thereof.

2. A compound according to claim 1, said compound being 3,4-dihydroxybenzohydroxyamidoxime.

3. A compound according to claim 1, said compound being 3,4,5-trihydroxybenzohydroxyamidoxime.

4. A compound according to claim 1 in which n is 3 and the three hydroxyls are in the 2, 3 and 4 positions.

5. A compound according to claim 1 in which n is 2 and the hydroxyls are in the 2 and 3 positions.

6. A hydrochloride salt of a compound according to claim 1.

7. A compound according to claim 1 in which two of the hydroxyls are vicinal.

8. A compound according to claim 1 in which n is 2 and the two hydroxyls are in the 3 and 4 positions.

9. A compound of the formula

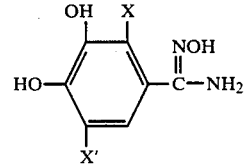

wherein X and X' are H or OH, but only one of X and X' can be OH in a given molecule, and pharmaceutically acceptable acid addition salts thereof.

10. A compound according to claim 9, said compound being 3,4-dihydroxybenzamidoxime.

11. A compound according to claim 9, said compound being 3,4,5-trihydroxybenzamidoxime.

12. A compound according to claim 9, said compound being 2,3,4-trihydroxybenzamidoxime.

13. Ethyl 3,4,5-trihydroxybenzamidate.

14. A method of inhibiting ribonucleotide reductase which comprises administering to a mammal carrying a tumor having a relatively high ribonucleotide reductase level, an amount of a compound according to the following formula effective to inhibit ribonucleotide reductase

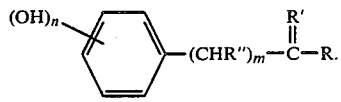

wherein n is 2–5; m is 0 or 1, R" is H or OH, R' is NOH or NH; R is $NH_2$ or NHOH when R' is NOH; R is $NH_2$ or O—$C_{1-3}$ alkyl when R' is NH; with the proviso that, when m is 0 and R' is NOH, R cannot be $NH_2$; or a pharmaceutically acceptable acid addition salt thereof.

15. A method according to claim 14 in which two of the OH groups in the phenyl ring are vicinal.

16. A method according to claim 14 in which m is 0.

* * * * *